(12) United States Patent
Newman

(10) Patent No.: US 7,807,717 B2
(45) Date of Patent: Oct. 5, 2010

(54) PESTICIDE FOR INSECT CONTROL

(75) Inventor: William A. Newman, Brooklyn Center, MN (US)

(73) Assignee: Remediation and Natural Attenuation Services Inc, Brooklyn Center, MN (US)

( * ) Notice: Subject to any disclaimer, the term of this patent is extended or adjusted under 35 U.S.C. 154(b) by 1041 days.

(21) Appl. No.: 11/169,427

(22) Filed: Jun. 29, 2005

(65) Prior Publication Data

US 2006/0008495 A1    Jan. 12, 2006

Related U.S. Application Data

(60) Provisional application No. 60/585,933, filed on Jul. 7, 2004.

(51) Int. Cl.
*A01N 37/16* (2006.01)
*A01N 37/18* (2006.01)
(52) U.S. Cl. ...................................... 514/552
(58) Field of Classification Search ................ 514/552
See application file for complete search history.

(56) References Cited

U.S. PATENT DOCUMENTS

| | | | | |
|---|---|---|---|---|
| 3,590,119 A | * | 6/1971 | Cardarelli et al. | 424/409 |
| 6,001,382 A | * | 12/1999 | Levy | 424/405 |
| 6,156,833 A | * | 12/2000 | Rauls | 524/239 |
| 6,281,189 B1 | * | 8/2001 | Heimann et al. | 510/491 |
| 7,048,918 B2 | * | 5/2006 | Warner et al. | 424/84 |

* cited by examiner

*Primary Examiner*—Johann R Richter
*Assistant Examiner*—Courtney Brown
(74) *Attorney, Agent, or Firm*—Bernd W. Sandt

(57) ABSTRACT

A method for the control of insects breeding on water surfaces and particularly mosquitoes, comprising blending in a high shear mixer water, the ester of a fatty acid of 10 to 25 carbon atoms and a low molecular weight alcohol, such as methanol or ethanol, an emulsifying agent and a thickener until an emulsion containing the ester with droplet sizes ranging from 1 to 20 microns in diameter is obtained and applying such to the surface of insect infested water in sufficiently diluted form, to break the emulsion and form a thin continuous film.

16 Claims, No Drawings

PESTICIDE FOR INSECT CONTROL

This application is a continuation-in-part of pending provisional application Ser. No. 60/585,933 filed Jul. 7, 2004.

FIELD OF INVENTION

The present invention relates to compositions used in controlling mosquito and similar insects that breed in or on standing water surfaces by delivering innocuous organic esters of fatty acids, in a thin, uniform film on surfaces of such standing water. The esters are applied as an emulsion, which breaks when in contact with the surface of the water to form a thin continuous film. The oil in the emulsion forms a thin film on the surface that blocks the breathing tubes of mosquito larvae and thereby kills them.

BACKGROUND

The use of fresh water ponds for watering stock has been a benefit to the ranchers in this country. However the breeding of mosquitos that carry the West Nile Virus in such ponds has also been a serious problem. Mosquitos and other biting insects can be a nuisance interfering with work and leisure time, and can cause the reduced production of milk and meat in livestock. Some mosquito species are capable of transmitting diseases to humans and/or animals including malaria, yellow fever, filarias, encephalitis, and West Nile virus.

The use of oil films on water surfaces to kill mosquito larvae is also well established and has been used for many years. Because of their adverse environmental impact petroleum fuel products such as diesel fuel, used initially as thin film larvicides have now been replaced by less toxic organic oil Examples. Modern commercial mosquito control products include highly refined mineral oils and organic acid surfactants that form films when applied to the water surface.

Fatty acid esters have been found to be a desirable choice since they are environmentally safe, have a relatively low viscosity, and can form continuous films on water surfaces that act as larvicides. The problem with the application of pure fatty ester oils has been that they tend to coalesce into large droplets rather than forming a continuous film, unless applied at high application rates. Adding surfactants can aid in dispersing of the methyl esters, but still results in incomplete surface coverage.

The use of oil-in-water emulsions is one method that looks promising for dispersing the oil phase as a continuous thin film. Oil-in-water emulsions with droplets that are small enough to produce kinetically stable emulsions will not cream to form a uniform surface film. Oil-in-water emulsions with large droplets will readily cream to form a continuous oil film, but will not be stable in dilute emulsions with a water external phase during storage of the product, making for a very limited shelf life.

By making a concentrated emulsion with 50% oil-in-water and adding a thickening agent to the water phase the emulsion can be made stable as a concentrate with good product shelf life, but when applied to the water surface the emulsion dilutes and breaks to form an effective oil film for mosquito control. The present invention provides oil-in-water emulsions of esters of fatty acid that are both stable prior to use in concentrated form and yet when applied to the water surface can break to form thin continuous film layers on the surface of water that are effective as larvicides.

BRIEF DESCRIPTION OF THE INVENTION

The present invention comprises the use of aqueous emulsions of esters of fatty acids with low molecular weight alcohols as a natural insecticide wherein the dispersed oil phase has droplet sizes ranging from 1 to 20 microns. In addition they contain one or more surfactants capable of emulsifying the fatty acid esters, and also contain a thickening agent as a stabilizer for the emulsion in concentrated form. Emulsions with the majority of droplets ranging between 2 microns and 10 microns are ideally suited for this purpose since they can be suspended for several hours in dilute form, but will cream out within hours or days when allowed to stand as a dilute emulsion in water. When spread on water the emulsions of the present invention destabilize as the thickening agent is diluted and the viscosity of the external phase of the emulsion decreases. These diluted emulsions form continuous thin layers of the ester, which are capable of killing mosquito larvae and similar insects that breed in such water. In another embodiment of the present invention the emulsions of the present invention serve as carriers for chemical insecticides that are used in insect control.

DETAILED DESCRIPTION OF THE INVENTION

The fatty esters used in the present invention are esters of saturated or unsaturated organic acids having from 10 to 25 carbon atoms and preferably 16 to 20 carbon atoms. The alcohols used in the esters are alcohols having from 1 to 6 carbon atoms and are preferably the methyl and ethyl esters. The fatty acids of the present invention are found in naturally occurring organic oils such as soybean oil, peanut oil, olive oil, cottonseed oil, linseed oil, coconut oil, rapeseed oil, and corn oil. The oils derived from seed are preferred. The primary acids contained in these oils are oleic and linoleic acid. The fatty acids are present in these seed oils as glyceride esters such as triglycerides. The alcohol esters used in the present invention are generally obtained through known transesterification by reaction with the desired alcohol. The most preferred fatty esters used in the present invention are the methyl and ethyl esters obtained by the transesterification of soybean oil with methyl or ethyl alcohol, generally referred to as methyl and ethyl soyate. The esterification is normally achieved by adding methanol to soybean or canola oil and heating the mixture with a catalyst to produce glycerin and methyl esters (methyl soyate).

The emulsions are preferably prepared such that the emulsion contains from 20 to 70% of the organic phase. When applied to a water surface the concentration of the organic phase is generally reduced to 1 to 10% by weight of the emulsion, which reduces the viscosity of the water phase, and causes the emulsion to break and form a thin continuous film on the water surface. Any standard mixer that provides sufficient shear to cause the formation of an emulsion with droplet diameters between 1 to 20 microns is suitable to prepare the emulsions of the present invention. Specific blenders useful for commercial production of the emulsions include the line of Ross rotor-stator mixers, which are commercially available.

A large number of emulsifying agents useful in the present invention are known to those skilled in the art and have been published in the literature. The affinity of an emulsification agent for water vs. oil is defined by its hydrophilic/lipophilic balance (HLB). The fatty esters used in the present invention are relatively easy to emulsify in water and a wide range of emulsification agents may be used with HLB values ranging from 8 to 15. Too low an HLB may result in production of a water-in-oil emulsion rather than an oil-in-water emulsion. Too high an HLB may result in problems with foaming.

Surfactants with differing HLB values may be blended to produce an additive average such that a blend of 50% by weight of a material with an HLB of 8 with 50% by weight of a material that has an HLB of 12 will produce a blend with an HLB of 10. Common food grade emulsifiers include lecithin, mono and diglycerides, mono and diglyceride ethoxylates, "Tweens" (polysorbates, a.k.a polyoxyethylene sorbitan esters), "Spans" (sorbitan esters), and glycerol esters.

The amount of emulsification agent can vary from 0.25% to 10% by weight of the fatty ester. More than one surfactant can be employed. The specific amount of emulsification agent should be selected such that it will allow an emulsion to be formed but also that once the emulsion is diluted and applied to the water surface the emulsion will break and form a continuous film on the surface. This will vary with the particular fatty ester employed and with the concentration in which it is employed. Suitable concentrations are however readily established by simple tests in which the emulsions are applied to water surfaces. To reduce regulatory concerns about toxicity biodegradable, food grade emulsifiers are preferred. Particularly suitable are blends of two or more emulsification agents that in combination produce an HLB between 10 and 12. Examples include lecithins, polysorbates, mono and diglycerides, sorbitan esters or mono and diglyceride ethoxylates.

The thickeners employed in the compositions useful in the present invention exhibit non-Newtonian behavior such that they impart a high viscosity to the aqueous medium in which they are employed, but act as a lower viscosity fluid when subjected to high shear forces such as in the spray application methods and equipment used in the process of the present invention. They are preferably organic in nature and biodegradable without harm to the environment. Suitable thickening agents include cornstarch, methylcellulose based thickeners and xanthan gum. The concentration of the thickener can vary depending on the relative potency of the thickening agent, the concentration of the fatty acid ester and the emulsifying agent employed but can readily be established experimentally. In most applications the concentration will vary between 0.05 and 5% by weight of the emulsion to which the thickener is added.

The concentration of emulsion necessary to achieve a practical degree of mortality of mosquito larvae will vary from 1 to 12, and preferably from 2 to 6 gallons, of the fatty acid ester per acre of surface water. The above application rate can be calculated based on the portion of water surface treated, rather than the total area of the lake or pond. Often in ponds and lakes mosquito larvae are concentrated near the shore sheltered by aquatic vegetation or small bays on the waters edge down wind of the prevailing wind direction. Treating the large open water areas away from the shore or the shoreline on the upwind side of the prevailing winds is often of little value. The fatty acid esters used in the present invention are more effective at higher concentrations although too high concentrations may be deleterious to wildlife and fish populations in the water. The fatty ester is applied in sufficient concentration to maintain the thin continuous layer for several days to several weeks. The oil film is most effective on the first four instars and pupae with an effective kill completed within the first three days after application A methyl soyate oil film that persists for weeks has the potential to kill a second hatch of mosquito eggs when they emerge as larvae. The methyl soyate surface film can also trap mosquitos that come to lay their eggs on the water surface or adult mosquitos that have just emerged on the surface of the water from pupa Field trial indicated that the emulsion could also kill other adult flies such as midges.

The emulsions used in the process of the present invention can also be used advantageously as carriers for chemical insecticides such as pyrethroids, organophosphates, and microbial agents such as Bacillus thuringiensus israelensis. These insecticides are preferably dissolved in the nonaqueous phase and are preferably added to the nonaqueous phase prior to the formation of the emulsion. Concentrations depend on the efficacy of the insecticide but generally are known for each insecticide.

The emulsions of the present invention can be reduced in microbial spoilage and have the product shelf life improved by pasteurization or by the addition of a food grade acid, such as citric acid, to lower the pH to below 3. At such pH levels known acid compatible surfactants are preferably used. When used as carriers for chemical added insecticides, the emulsions of the present invention can be stabilized with known ultraviolet light stabilizers, such as carbon black, titanium dioxides and aromatic organic compounds to prevent photo degradation of insecticide additives.

The invention is illustrated by the following examples.

EXAMPLE 1

The oil phase of the emulsion was first prepared from methyl soyate, and surfactant consisting of 320 g of commercially available methyl soyate, 12.5 g of a polysorbate 60, and 12.5 g of cc280 (a dry powder blend of 80% mono and diglycerides with 20% polysorbate 80 from Custom Continental Ingredients). The HLB of the surfactant blend is approximately 11. Water and a thickening agent were prepared from 100 ml of water and 10 g of cornstarch. 100 ml of the methyl soyate surfactant mix was added to the water and cornstarch and the resulting mixture was heated to 70° C. to activate the starch, and processed at low speed in a blender to simulate the shear of a rotor-stator inline mixer. The resulting emulsion had a median droplet size of 2.154 microns by volume and droplets were detected ranging from 0.339 microns to as large as 15.172 microns.

The concentrated emulsion showed non-Newtonian viscosity behavior with values ranging from 370.5 centipoises to 1205 centipoises at 60 rpm and 6 rpm respectively (Brookfield Viscometer). Pan tests were conducted by applying the emulsion to test pans containing 300 $4^{th}$ stage mosquito larvae. In a 72-hour test an LC50 (50% larval mortality) was achieved at an application rate of 6.25 gallons per acre and an LC70 (70% mortality) was achieved at a 10.42-gallon rate of emulsion per acre.

With the above droplet size range some of the droplets under one micron in size are less likely to cream from the dilute emulsion. To optimize the Example a larger droplet size was targeted by reducing the amount of surfactant, and more efficient thickening agents were utilized to reduce the percentage of thickener necessary to stabilize the emulsion.

The following test formulations were prepared to test alternative thickening agents and a smaller percentage of surfactant The surfactant consisted of equal amounts of cc280 and polysorbate 60 with a final HLB of approximately 11. Formulations using 60% to 70% of methyl soyate were tried successfully at surfactant concentrations of about 5%. The methyl soyate employed was "Soy Gold 1000" from AP Environmental Products and the thickening agents were xanthan gum from Aldrich and hydroxymethyl cellulose, "Natrasol 250 HR", from Hercules. All of the formulations were processed with a "Gifford" 1.51 bench-top rotor stator mixer for three minutes at 50% power approximating the processing conditions used with full scale production high shear mixers. All viscosity measurements were made with a Brookfield Viscometer at 5-100 rpm.

EXAMPLE 2

500 ml water, 500 ml methyl soyate, 1.5 g xanthan gum, 5 g surfactant resulted in an emulsion having a median droplet size of 5.3451 microns, a droplet size range from 1.151 to 13.246 microns, viscosity of 226-1280 centipoises on processing and on two week storage a viscosity of 282-1360 centipoises.

EXAMPLE 3

500 ml water, 500 ml methyl soyate, 1.35 g xanthan gum, 10 g surfactant resulted in an emulsion having a median droplet size 3.3487 microns, a droplet size range from 1.510 to 7.697 microns, a viscosity 250-950 centipoises on processing and on two week storage a viscosity of 196-1000 centipoises.

EXAMPLE 4

500 ml water, 500 ml methyl soyate, 1.6 g xanthan gum, 10 g surfactant resulted in an emulsion having a median droplet size of 5.1941 microns, a droplet size range from 0.669 to 13.249 microns, an viscosity of 286-1800 centipoises.

EXAMPLE 5

500 ml water, 500 ml methyl soyate, 1.5 g xanthan gum, 10 g surfactant resulted in an emulsion having a median droplet size 5.1075 microns, a droplet size range from 1.151 to 11.565 microns, a viscosity 260-1320 centipoises on processing and a range of 238 to 1360 centipoises on two weeks storage.

EXAMPLE 6

500 ml water, 500 ml methyl soyate, 1.5 g xanthan gum, 25 g surfactant resulted in an emulsion having a median droplet size of 3.9010 microns, a droplet range from 1.318 to 10.097 microns, a viscosity of 258-1480 centipoises on processing and a viscosity of 170-1600 centipoises on two weeks storage.

EXAMPLE 7

500 ml water, 500 ml methyl soyate, 3.9 g Natrasol (a hydroxymethyl cellulose thickener), 10 g surfactant resulted in an emulsion having a median droplet size of 4.0940 microns, adroplet range from 1.510 to 10.097 microns, a viscosity 334-860 centipoises on processing and a viscosity of 175-680 centipoises after two weeks storage.

EXAMPLE 8

500 ml water, 500 ml methyl soyate, 4.8 g Natrasol (a hydroxymethyl cellulose thickener), 10 g surfactant resulted in an emulsion having a: median droplet size of 5.6329 microns, a droplet range from 0.766 to 13.246 microns, a viscosity of 483-1340 centipoises on processing and 252 to 1160 centipoises on two weeks storage.

EXAMPLE 9

500 ml water, 500 ml methyl soyate, 5.44 g Natrasol (a hydroxymethyl cellulose thickener), 10 g surfactant resulted in a median droplet size of 4.7761 microns, a droplet range from 1.005 to 10.097 microns, a viscosity 661-2100 centipoises on processing and 450-2000 centipoises on two weeks storage.

Droplet size was determined by volume distribution using a laser diffraction instrument Viscosity was determined using a Brookfield Viscometer with spindle speeds ranging from 5 to 100 rpm In all cases the test samples exhibited a non-Newtonian viscosity with decreasing viscosity measured at increasing spindle speeds. All of the above test examples were stable and showed no sign of creaming in concentrated form For accelerated gravity separation testing the samples were centrifuged and again showed no signs of gravity separation by creaming. All of the above test formulations have good properties for use as larvicide sufficant.

EXAMPLE 10

A 30 gallon production run was conducted using the following formulation: 48.1% weight Methyl Soyate (Soy Gold 1000), 48.1% weight distilled water, 0.96% surfactant (equal amounts of polysorbate 60 and CC280), 0.13% xanthan gum, 1.3% Citric Acid, and 1.4% Sodium Citrate. This test formulation is the same as Example 3, but with a citrate buffer added to lower the pH to reduce microbial spoilage and improve shelf-life without refrigeration. Immediately after processing the emulsion was tested for particle size by laser diffraction methods. Oil droplets ranged from 1.32 to 11.6 microns with an average particle size of 4.60 microns. Viscosity was measured with a Brookfield viscometer with spindle speeds ranging between 5 and 100 rpm. The emulsion exhibited a non-Newtonian viscosity with values ranging between 262 and 1,520 centipoises.

Five of the 5-gallon pails were set aside for shelf life testing. The material was not pasteurized so the reduced pH from the citric acid/citrate buffering system was the only preservative to reduce microbial spoilage. The xanthan gum thickening agent proved effective in preventing oil/water separation in emulsion samples that had no sign of microbial spoilage. Of the five pails that were sampled approximately one year later, four of the five had minor evidence of microbial spoilage, with small quantities of mold visible on the tops of the emulsion pails after storage without refrigeration for a period of almost one year.

The pail that had no evidence of mold had no evidence of any oil/water separation and was tested for particle size and had essentially the same properties as the original production run with the exception of a trace amount of oil droplets larger than 12 microns (about 2.2% by volume) with oil droplets ranging from 1.00 microns to 22.8 microns with an average oil droplet size of 5.37 microns by volume distribution as determined by a laser diffraction method. Viscosity was measured with a Brookfield viscometer at 5-100 rpm and exhibited a non-Newtonian viscosity ranging from 208 centipoises to 1160 centipoises. The thickening agent appeared to be very effective in stabilizing the emulsion even where microbial spoilage impacted the surfactants. Acidification alone did not prove an adequate protection from all microbial spoilage for storage for a year without refrigeration and indicated the need for pasteurization for long-term stability.

EXAMPLE 11

Four small ponds on a ranch in Wyoming were identified for test locations and floating boom dividers were used to further subdivide the ponds into five test areas. An initial survey of the test areas was conducted for both aquatic insects and vegetation. Insects were sampled using dip nets within two meters of the shore within the emergent vegetation, which produces ideal mosquito habitat The predominant mosquito larvae identified was *Culiseta inornata*, and field observations indicated that 96% of the mosquito larvae were present within one meter of the shore. Field observations indicated that much of the aquatic habitat for the mosquito larvae consisted of small pools and deep tracks from cattle that did not connect with the main body of water. On August 9-10 the plots were sampled and large population of larvae was observed with 1095 larvae counted in the control plots and 1631 counted in the treatment plots.

The test plots were treated with 2.5 gallons per acre of emulsion of Example 10, with the Control Plots remaining untreated. After 24 hours the plots were sampled again with 1200 larvae found in the Control Plots and only 25 identified in the treatment area where 2.5 gallons per acre of emulsion had been applied. Based on this first application trial there was a 24 hour kill of the *Culiseta inornata* larvae in excess of 98% from the emulsion treatment. Results were quite consistent with kill rates of 99.2%, 99.0%, 95.95%, 99%, and 98% for the five test areas. Larvicide efficacy at a given application rate for EPA registration purposes is generally defined as having a 95% kill rate within 72 hours of application.

Kill rates of non-target insect species were a total of 326 non-target insects killed within the five test plots. Most consisted of adult flies (*Diptera*) with the vast majority consisting of adult *Chironomidae* (gnats and midges), 198 killed in the five test plots. Although these gnats and midges are not a disease vector like the mosquito they are a nuisance to the cattle and ranchers, such that larvicide may have pest control applications for control of adult *Chironomidae* as they lay their eggs on the surface of the water or in capturing adults as they emerge from the ponds and become trapped in oil film at the waters surface. An additional 86 insects consisted of other *Diperta* such as houseflies, deer flies, etc. Of the 326 non-target species killed only 42 consisted of non-pest insects such as diving beetles, water boatmen, dragon flies, may flies and damsel flies.

A month later a second survey and treatment trial was conducted using the same treatment and control areas. Although the emulsion treatment had been effective in killing over 98% of the *Culiseta inonata* mosquito larvae, the treatment test plots had now been colonized by another mosquito species *Culex tarsalis*. The Control area had a count of 1702 mosquito larvae and the treatment area had a count of 3,440 larvae. 2.5 gallons per acre of emulsion of Example 3 was added to the treatment areas, while the control was left untreated. On the next day the control area had a count of 1,945 mosquito larvae while the treatment area had only 59 mosquito larvae. With *Culiseta inonata* there appeared to again be a larval kill of over 98% in 24 hours. Kill rates for non-target insects followed a similar pattern to the first treatment with 479 non-target insects killed and of those 463 consisted of adult midges (*Chironomidae*) and flies (*Diptera*).

The invention claimed is:

1. A method for the control of insects breeding on water surfaces, consisting essentially of the steps of (1) blending in a high shear mixer, the ester of a fatty acid of 10 to 25 carbon atoms and a low molecular weight alcohol, an emulsifying agent and a thickener and water, such that the organic phase comprises from 20 to 70% by weight of the mixture until an emulsion containing the ester with droplet sizes ranging from 1 to 20 microns in diameter is obtained (2) diluting the organic phase of the emulsion to a concentration of 1 to 10% by weight of the emulsion and (3) applying such to the surface of insect infested water in a concentration of 6 to 12 gallons of fatty acid ester per acre of surface water, thereby breaking the emulsion to form an oil film on the water.

2. The method of claim 1 wherein the insects are mosquitoes.

3. The method of claim 1 wherein the fatty acid of the ester is derived from seed oil and the alcohol has from 1 to 6 carbon atoms.

4. The method of claim 1 wherein the fatty acid of the ester is derived from vegetable oil and the alcohol is methyl or ethyl alcohol.

5. The method of claim 1 wherein the thickener or thickeners are a food grade material selected from the class consisting of corn starch, xanthan gum and cellulose derivatives.

6. The method of claim 1 wherein the emulsion is formed in a rotor-stator high shear mixer.

7. The method of claim 1 where the ester of the fatty acid is the methyl or ethyl ester of the fatty acid of soybean oil.

8. The method of claim 1 wherein the emulsion contains the methyl or ethyl ester of the fatty acid of canola oil.

9. The method of claim 1 where the emulsion contains a food-grade surfactant or surfactant blend with an HLB value of 8 to 15 and 0.1 to 5% surfactant by weight of the alcohol ester.

10. The method of claim 1, where the thickening agent is applied to the emulsion to produce a low shear viscosity between 200 and 2,000 centipoises.

11. The method of claim 1, wherein the emulsion is heated to pasteurize the product for resistance to microbial spoilage.

12. A method for the control of mosquito larvae breeding on water surfaces, consisting essentially of (1) forming an emulsion by blending in a high shear mixer the methyl or ethyl ester of a fatty acid derived from soy been, peanut, olive cottonseed linseed, coconut rape or corn oil, a food grade emulsifying agent having an HLB value of 8 to 15 in a concentration of 0.1 to 5% and a food grade thickener in a concentration of 0.05 to 5% and water, such that the organic phase comprises from 20 to 70% by weight of the mixture until an emulsion containing the ester with droplet sizes ranging from 1 to 20 microns in diameter is obtained (2) diluting the organic phase of the emulsion to a concentration of 1 to 10% by weight of the emulsion and (3) applying such to the surface of insect infested water in a concentration of 6 to 12 gallons of fatty acid ester per acre of surface water to result in an oil film on the water.

13. The method of claim 12, wherein the thickener is selected from the class consisting of corn starch, xanthan gum and cellulose derivatives.

14. The method of claim 12, wherein the ester of the fatty acid is derived than soybean oil.

15. The method of claim 12, wherein the thickening agent is added to the emulsion in a concentration sufficient to produce a low shear viscosity between 200 and 2,000 centipoises.

16. The method of claim 12, wherein the emulsion is heated to pasteurize the product for resistance to microbial spoilage.

* * * * *